United States Patent [19]

Eastman

[11] Patent Number: 5,474,718
[45] Date of Patent: Dec. 12, 1995

[54] STARCH HYDROLYSATES AS SEQUESTERERS

[76] Inventor: James E. Eastman, 444 S. Westdale Ave., Decatur, Ill. 62522

[21] Appl. No.: 14,770

[22] Filed: Feb. 8, 1993

[51] Int. Cl.$^6$ .............................. B01J 13/02; A61K 9/62; C08B 37/16; C13K 1/06
[52] U.S. Cl. ................ 264/4.3; 127/38; 252/174.13; 252/180; 252/351; 424/493; 428/402.2; 426/98; 426/654; 426/661; 536/103
[58] Field of Search .......................... 252/351, 174.13; 264/43; 428/402.2; 127/38; 426/98, 654, 661; 424/493; 536/103

[56] References Cited

U.S. PATENT DOCUMENTS

| | | | |
|---|---|---|---|
| 2,827,452 | 3/1958 | Schlenk et al. | 536/103 X |
| 3,799,805 | 3/1974 | Sugimoto | 127/38 |
| 3,974,032 | 8/1976 | Harjes et al. | 426/661 X |
| 4,285,983 | 8/1981 | Saldarini et al. | 426/534 |
| 4,465,702 | 8/1984 | Eastman eet al. | 426/578 |
| 4,728,510 | 3/1988 | Shibanai et al. | 428/402.2 X |
| 4,812,445 | 3/1989 | Eden et al. | 514/60 |
| 4,837,314 | 6/1989 | Eastman | 536/111 |
| 4,869,904 | 9/1989 | Uekama et al. | 536/103 X |
| 5,037,929 | 8/1991 | Rajagopalan et al. | 426/578 |
| 5,070,081 | 12/1991 | Majid et al. | 536/103 X |
| 5,275,837 | 1/1994 | Eastman | 426/661 |

OTHER PUBLICATIONS

R. Whistler et al (Eds.), *Starch: Chemistry and Technology*, 2d Ed., Academic Press, Inc. (1984), pp. 154–155 and 260.
Jay–lin Jane, *Trends In Food Science & Technology*, Jun. 1992 (vol. 3), pp. 145–148.
J. Jane et al., *Starch/Stärke*, 38 (1986), No. 8, pp. 258–263.
"A Granular Cold Water–Soluble Starch Gives A V–Type X–Ray Diffraction Pattern", J. Jane, et al., *Carbohydrate Research*, 150 (1986) C5–C6.
"Starch Derivative Cyclodextrin: Novel Properties For Multi–Niche Market Will Grow To $245 Million In U.S.", *Bioprocessing Technology*, Nov. 1987, pp. 4–5.
"Recent Advances In The Use Of Cyclodextrins in Food Systems", R. B. Friedman, et al., American Maize–Products Company, Hanmond, Indiana, pp. 74–82; Frontiers in Carbohydrate Research Elsevier Science Publ. Co. (1989).
"Cyclodextrins Debitter Citrus Juices", R. J. Swientek, *Food Processing*, Jul. 1988, pp. 54–55.
"Encapsulating Of Artificial Flavors By β–Cyclodextrin", G. A. Reineccius, et al., *Perfumer & Flavorist*, vol. 11, Aug./Sep. 1986, pp. 2–6.
"Production And Potential Food Applications Of Cyclodextrins", *Food Technology*, Jan. 1988, pp. 96–99.
"Thymol and Cyclohexanol As Fractioning Agents For Starch", Bourne, E. J., et al., *Journal of the Chemical Society*, 1948, pp. 1687–1693.

*Primary Examiner*—Richard D. Lovering
*Attorney, Agent, or Firm*—Barnes & Thornburg

[57] ABSTRACT

A starch hydrolysate composition is particularly suited for use as a sequesterer, i.e., it readily interacts noncovalently with other molecules to form stable inclusion complexes which are useful in a variety of applications. The starch molecules in the composition which act as sequesterers are in the form of single helical inclusion complexes with starch molecules having a D.P. of about 10 to 200 and a weight-average D.P. of about 10 to 50 as the host molecule holding one or more guest molecules within their internal cavities. These hydrolysates are prepared by first converting amylopectin molecules from the double helix form to the single helix form and then by cleaving chain segments from the molecules.

10 Claims, No Drawings

STARCH HYDROLYSATES AS SEQUESTERERS

FIELD OF THE INVENTION

This invention relates to starch hydrolysates. More specifically, this invention relates to starch hydrolysates particularly suited for use as sequesterers.

BACKGROUND OF THE INVENTION

A sequesterer is a compound which is able to interact noncovalently with other molecules to form stable inclusion complexes. A well known class of sequesterers are the three cyclodextrins: α-, β-, and γ-cyclodextrin which contain, respectively, six, seven, and eight anhydroglucose ($C_6H_{10}O_5$) units. These molecules are doughnut-shaped rings having a hollow cavity of a specific volume. The polar hydroxyl groups are oriented to the outside of the rings, giving the outer surface a hydrophilic nature. In contrast, the internal cavity has a hydrophobic (lipophilic) nature. Because of this unique structure, cyclodextrins, as the "host" molecules, are able to hold "guest" molecules of suitable size (generally of a molecular weight between 80 and 250), shape, and hydrophobicity within their cavity. Although cyclodextrins are very expensive to produce and are of limited availability, a number of important sequestering uses have been discovered for them. See, e.g., D. E. Pszczola, "Production and Potential Food Applications of Cyclodextrins," *Food Technology*, January 1988, pp. 96–100. It would be very desirable to provide sequesterers that are easily produced and that accommodate guest molecules of widely-varying size, shape, and hydrophobicity.

Cyclodextrins are derivatives of starch, a plant material formed of anhydroglucose polymers. Starch is a member of the class of compounds known as polysaccharides in that it contains three or more saccharide units. It is also a member of the broader class of compounds known as carbohydrates. Starch occurs naturally in plants in the form of granules having an average size of about 5 to 100 microns and containing thousands of individual starch molecules bound tightly together. Starch molecules exist as lightly-branched chains consisting predominantly of α-1,4-linkages between the anhydroglucose units, known as amylose, and as highly-branched chains consisting of both α-1,4- and α-1,6-linkages, known as amylopectin. Differences between amylose and amylopectin have been studied by first rupturing the starch granule and then separating the two fractions. This separation is often accomplished by precipitating amylose as a complex with butanol. Amylose has also been reported to form complexes with aliphatic alcohols such as isopropyl and isoamyl, as well as a variety of other organic compounds. R. Whistler et al. (eds.), *Starch: Chemistry and Technology*, 2d ed., Academic Press, Inc., 1984, pp. 154–155 and 260.

Based on these, and other, studies, it is believed that amylopectin grows in clusters having a length of about 50 to 70 Angstroms. Additional studies have led to the discovery that the amylopectin molecule contains three distinct types of chains which have been designated as A-chains, B-chains, and C-chains. See D. Manners, "Recent Developments in Our Understanding of Amylopectin Structure," *Carbohydrate Polymers*, Vol. 11, 1989, pp. 87–112. The single C-chain contains the only reducing group of the molecule and is the chain from which all other chains branch. B-chains are linked to two or more other chains. A-chains are bound to only one other chain. It is believed that A-chains contain about 12 to 16 anhydroglucose units and are generally confined to individual clusters. B-chains show modality in their size distribution. Three modes, which are designated $B_1$, $B_2$, and $B_3$, comprise most of the B-chains and average about 22, 45, and 70 anhydroglucose units, respectively. It is believed that the $B_1$ fraction is confined to a single cluster, but that the other B-fractions extend into other clusters. A fourth mode of B-chains, which are as long as 200 anhydroglucose units and which extend beyond three clusters, have been found and are designated $B_4$.

The exact structure of starch on a molecular level is still under investigation. It is believed that at least some unmodified starch exists on a molecular level in the form of a double helix-two, long, winding chains in close association with each other. Various theories regarding the nature of this association have been postulated: some scientists believe the chains are intertwined in a parallel arrangement while others believe that the chains are intertwined in an antiparallel arrangement. It is also believed that, at least in some types of starch, a portion of the amylose exists in the form of a single helix inclusion complex-a single winding chain containing six anhydroglucose units per turn wrapped around a lipid molecule. See T. Galliard, *Starch: Properties and Potential*, John Wiley & Sons, 1987, pp. 69–75.

One method frequently used to investigate the structure of the starch molecule is to observe its response to exposure to electromagnetic radiation. When unmodified starch is exposed to polarized light, it exhibits a birefringence (judged empirically by the presence of a characteristic "Maltese Cross" pattern) indicating an orderly, crystalline-like structure. It is believed that the amylopectin fraction of starch is primarily responsible for this crystallinity.

Starch also exhibits characteristic diffraction patterns when exposed to x-ray radiation. Cereal starches exhibit a pattern identified as the A-pattern, tuber and root starches exhibit the so-called B-pattern, and starches of the Liguminosae family exhibit the C-pattern (there is no relationship between the use of the letters A, B, and C in connection with types of chains and the use of the same letters in connection with types of diffraction patterns, i.e., an A-chain does not imply an A-diffraction pattern). It is believed that the single helix amylose inclusion complexes present in some unmodified starches generate a V-pattern, but it is not discernible because of the limited presence of these complexes. Id. at 74.

Returning to the macro level, unmodified starch granules are insoluble in cold water, but can be dissolved by heating in water at a temperature of about 70° to 90° C. at atmospheric pressure. At this point the granules gradually swell and rupture and the individual molecules pass into solution. This process by which starch granules swell and rupture is alternatively referred to as gelatinization, pasting, or cooking. As the starch gelatinizes, its crystallinity disappears and its birefringence is lost. It is believed that, during gelatinization, those starch molecules existing in the form of a double helix disengage to form two single-stranded polymer chains.

The major commercial source of starch is corn (also known as maize), but potatoes, wheat, barley, rice, and tapioca are also important sources. The relative amounts of amylopectin (branched chains) and amylose (primarily unbranched chains), as well as the average number of anhydroglucose units in a molecule (commonly known as the *Degree of Polymerization*, or D.P.) varies with the species of plant. For example, common dent corn starch contains about 72% amylopectin and 28% amylose; waxy maize corn starch contains nearly 100% amylopectin; and a common high amylose corn starch contains about 45% amylopectin and 55% amylose (all percentages are given on a weight-percent basis unless otherwise indicated). Corn starch amylopectin has a D.P. of about 300,000 to 3,000,000 while amylose has a D.P. of about 800 to 8,000.

Corn starch is often modified chemically to alter its physical properties for a given application. One common modification is to substitute other chemical groups onto the hydroxyl groups of the starch molecules. The amount of substitution is expressed as the *Degree of Substitution*, or D.S. A starch molecule having one substituted group per anhydroglucose unit is defined as having a D.S. of one. A molecule having one substituent per 2 anhydroglucose units has a D.S. of 0.5., and so on. Another common modification is to treat the starch with an agent such as acid or enzyme to cleave some of the bonds between the anhydroglucose units to produce shorter chain segments and thereby reduce the average D.P. of the starch molecules. Starches having a reduced D.P. are said to be hydrolyzed or convertecL They are often described in terms of their *Dextrose Equivalent*, or D.E., which is defined for an individual molecule as 100÷D.P. Accordingly, the monosaccharide dextrose, also known as glucose, has a D.P. of 1 and a D.E. of 100. Dextrose Equivalent is a convenient measure of the sweetness of a starch derivative and is widely used in the corn refining industry. In a mixture of molecules having different D.P.'s, D.E. can be viewed as a non-weighted average of the D.E.'s of the individual molecules. Depending upon the population distribution, two mixtures having the same average D.P. can have different D.E.'s, as shown by the following example.

Assume mixture A contains 6 starch derivative molecules, each one having a D.P. of 2 and a D.E. of 50. The average D.P. of the mixture is, of course, 2: [(2+2+2+2+2+2)÷6] and the D.E. of the mixture is 50: [ (50+50+50+50+50+50 )÷6]. Now consider mixture B which also contains 6 molecules, but of the following distribution: The first molecule has a D.P. of 4 and a D.E. of 25; The second molecule has a D.P. of 3 and a D.E. of 33.33; The third molecule has a D.P. of 2 and a D.E. of 50; And the remaining three molecules each has a D.P. of 1 and a D.E. of 100. This mixture has an average D.P. of 2: [(4+3+2+1+1+1)÷6], the same as mixture A. But mixture B has a D.E. of 68: [(25+33.33+50+100+ 100+100)÷6], and would be sweeter to the taste than mixture A.

Although the cyclodextrins are the only starch derivatives currently used commercially as sequesterers, a large number of starch derivatives have been disclosed for other uses. For example, Eastman et al., U.S. Pat. No. 4,465,702, issued Aug. 14, 1984, disclose a cold-water-soluble, granular starch derivative prepared by heating ungelatinized starch in a slurry of selected aqueous alcohols under high pressure. Rajagopalan et al., U.S. Pat. No. 5,037,929, issued Aug. 6, 1991, disclose a granular cold-water-soluble starch prepared by heating a slurry of granular starch, water, and a polyhydric alcohol under atmospheric pressure. Both the Eastman et al. and Rajagopalan et al. starch derivatives exhibit a V-type x-ray diffraction pattern. See J. Jane et al., "A Granular Cold Water-Soluble Starch Gives A V-Type X-Ray Diffraction Pattern," *Carbohydrate Research*, Vol. 150, 1986, pp. C5-C6. Neither the Eastman et al. process nor the Rajagopalan et al. process significantly affects the D.P. of the starch molecules. These starch derivatives are alleged to be particularly useful in food systems of the type which set or gel upon standing. Sugimoto, U.S. Pat. No. 3,799,805, issued Mar. 26, 1974, discloses a process for producing granular dextrins. The dextrins are prepared by heating granular starch with acid in an aqueous solution of an organic solvent such as propanol, ethanol, methanol, acetone, and fatty acids. Sugimoto teaches that the resulting dextrins are useful in the production of maltodextrins.

SUMMARY OF THE INVENTION

A general object of this invention is to provide an improved sequesterer. Another general object of this invention is to provide an improved method of preparing a sequesterer. A further general object of this invention is to provide an improved method of sequestering a molecule.

I have invented a starch hydrolysate composition particularly suited for use as a sequesterer. The composition is characterized in that at least about 20% of the starch is in a sequestering form comprising single helical inclusion complexes of starch molecules having a D.P. of about 10 to 200 and a weight-average D.P. of about 10 to 50 as the host molecules holding one or more guest molecules within their internal cavities.

I have also invented a method of preparing a starch hydrolysate composition particularly suited for use as a sequesterer. The method comprises: (a) obtaining a granular starch containing at least about 30% amylopectin; (b) preparing a slurry of about 10 to 50% of the granular starch in a liquid medium which comprises about 60 to 90% of an organic non-starch solvent and about 10 to 40% of a starch solvent; (c) heating the slurry under conditions sufficient to convert at least a portion of the amylopectin molecules to the form of single helical inclusion complexes of starch molecules holding one or more of the non-starch solvent molecules as the initial guest molecules within their internal cavities; (d) heating the slurry under conditions sufficient to cleave enough chain segments from the amylopectin molecules such that at least about 20% of the starch is in a sequestering form comprising single helical inclusion complexes of starch molecules having a D.P. of about 10 to 200 and a weight-average D.P. of about 10 to 50 as the host molecules holding one or more first guest molecules within their internal cavities; and (e) separating the resulting starch from the liquid.

I have further invented a method of sequestering a molecule. The method comprises: (a) providing a starch hydrolysate composition characterized in that at least about 20% of the starch is in a sequestering form comprising single helical inclusion complexes having starch molecules with a D.P. of about 10 to 200 as the host molecules holding one or more first guest molecules within their internal cavities; (b) contacting the starch hydrolysate composition with a composition containing second guest molecules to be sequestered under conditions to displace the first guest molecules with the second guest molecules; and (c) separating the starch hydrolysate-guest molecule inclusion complex from the composition containing the second guest molecules and the displaced first guest molecules.

The starch hydrolysates of this invention are effective sequesterers. As such, they are suitable for many of the uses which have been discovered for cyclodextrins. Moreover, unlike the cyclodextrins, the starch hydrolysates of this invention are easily and inexpensively produced. They are also able to accommodate guest molecules of widely varying size, shape, and hydrophobicity.

DETAILED DESCRIPTION OF THE INVENTION

1. Conversion To Single Helical Form

In a simplified manner, the starch hydrolysate composition of this invention can be considered to be prepared by a two-step process. The first step is to heat a granular starch slurried in two miscible solvents, one of which is a solvent for starch and one of which is not, under conditions to convert the starch molecules to a single helix form. The second step is to heat the starch in an acidic slurry of the same two types of solvents under conditions to cleave chain segments from the amylopectin molecules. The product thus contains single helices of a relatively narrow D.P. range which are highly-effective sequesterers. These sequesterers are used as part of the starch hydrolysate composition or are separated from the rest of the composition prior to use.

The starch hydrolysates of this invention are chain segments derived from the amylopectin portion of granular starch. Therefore, the raw material for the starch hydrolysates is a granular starch containing at least about 30% amylopectin. The source of the starch is not critical and starches derived from corn, potatoes, wheat, barley, rice, tapioca, etc., and blends thereof are all suitable. The preferred raw material is a starch containing at least about 50% amylopectin. As the amount of amylopectin increases, the number of A-chains and B-chains increases and it is primarily these chains that are cleaved and transformed into the sequesterers. However, starches containing large amounts of amylopectin, such as waxy maize corn starch, are more difficult to process so it is not necessarily desirable to simply maximize the amount of amylopectin in the raw starch. The more preferred raw material is a starch containing about 60 to 90% amylopectin, and the most preferred raw material is a common dent corn starch containing about 72% amylopectin.

Mild chemical modification of the starch up to about 0.1 D.S. (1 substituent group per 10 anhydroglucose units) is acceptable. Chemical modification can influence the hydrophilic/lipophilic balance of the resulting starch hydrolysates. In particular, substituents such as octenylsuccinate or acetyl tend to enhance the lipophilic properties of the starch hydrolysates, while substituents such as hydroxyalkyl, carboxymethyl, or phosphate groups tend to enhance the hydrophilic properties. Accordingly, the choice of modification depends on the properties desired in the starch hydrolysates which, in turn, depends on the type of molecules to be sequestered.

The granular starch is heated in a slurry of at least two miscible solvents. For economic reasons, it is desirable that the slurry contain the maximum amount of starch that can be readily pumped. During the heating, the starch granules swell somewhat, making the slurry more viscous. The slurry generally contains about 10 to 50% starch and preferably contains about 15 to 25% starch, on a dry substance basis.

One of the solvents in the starch slurry is an organic solvent which does not dissolve starch. Suitable organic non-starch solvents include acetone and the lower-chain alcohols such as methanol, ethanol, n-propanol, and isopropanol, and mixtures thereof. The preferred non-starch solvents are ethanol and isopropanol. The most preferred non-starch solvent is ethanol because of its low toxicity and ready availability. Ethanol is generally available commercially in a denatured form. A preferred form of denatured ethanol is grade 3A which contains minor amounts of methanol and water. The liquid medium of the starch slurry also includes a solvent which does dissolve starch and which is miscible with the non-starch solvent. Suitable starch solvents include water, dimethyl sulfoxide, dimethyl formamide, N-methyl pyrrolidone, and 2-amino ethanol. Water is the preferred starch solvent because of its cost, ready availability, non-toxicity, and solvating ability. Of the liquid medium, the non-starch solvent generally comprises the major portion, preferably about 60 to 90%, and most preferably about 70 to 85%, with the starch solvent comprising all or most of the remainder of the liquid medium.

The cleavage of the $\alpha$-1,4- and $\alpha$-1,6-glycosidic bonds between the anhydroglucose units in the starch molecule is an acid-catalyzed reaction which is strongly temperature-dependent. Little or no cleavage occurs at near-neutral pH's and mild temperatures. At slightly lower pH's and slightly higher temperatures, cleavage of both types occurs, but the $\alpha$-1,6-cleavage predominates, thus favoring the cleavage of the chain segments at their branch points. At even more acidic conditions and at even higher temperatures, the $\alpha$-1,4-cleavage reaction increases relative to the $\alpha$-1,6-cleavage reaction. It is preferred that minimal cleavage of either type occur at the first stage and that the $\alpha$-1,6-cleavage of the chain segments predominate at the second stage. Accordingly, it is preferred that the slurry be at or near neutrality during the single-helix-conversion step. If the slurry is acidified, it is preferred that the Normality be less than about 1.5, more preferably less than about 1.0, and that a mineral acid such as sulfuric, phosphoric, or hydrochloric be used. Sulfuric acid is preferred because it is the least corrosive of the common mineral acids.

The slurry is heated under conditions which cause the amylopectin molecules to convert from the double helix to single helix form. It is preferred that all, or nearly all, of the amylopectin molecules be converted to the single helix form. An estimate of this conversion is obtained by viewing the starch under a polarized light microscope. Although total disappearance of the characteristic Maltese Cross pattern is not necessarily a guarantee of total conversion to the single helical form, it does assure sufficient conversion to produce an effective product. The temperature, pressure, and reaction time are inter-related variables in this conversion. Other things being equal, a higher reaction temperature increases the rate of conversion. In general, the slurry is heated at a temperature of about 70° to 180° C. at a pressure of about 1 atmosphere (atmospheric pressure) to 20 atmospheres. Because the reaction temperature is limited at atmospheric pressure by the normal boiling point of the slurry, it is necessary to maintain superatmospheric pressure to conduct the conversion at higher temperatures. Various processing equipment are suitable for the heating, including stirred tank reactors and tubular reactors. The conversion time varies from only a few seconds in a turbulent-flow, high-pressure, high-temperature tubular reactor to 30 minutes or more under milder conditions.

The processes described in Eastman et al., U.S. Pat. No. 4,465,702, issued Aug. 14, 1984, and in Rajagopalan et al., U.S. Pat. No. 5,037,929, issued Aug. 6, 1991, each of which is incorporated by reference, are also suitable for converting starch to the single helix form.

After the desired degree of conversion to the single helix form is completed, the slurry may be immediately processed to cleave the chain segments as described below. Alternatively, the slurry may be cooled and subjected to other processing prior to the cleavage step. For example, it is sometimes desirable to alter the slurry composition or to recover the starch.

It is believed that the single helices produced during this first step are inclusion complexes containing the organic non-starch solvents as their guest molecules. While not wishing to be bound by theory, it is believed that the double helix starch molecules are not, as previously theorized, intertwined as two parallel polymer strands around a common axis. Such intertwined chains would have to unwind from top to bottom to disengage, an unlikely process in view of the ease with which the double helix form converts to the single helix form in this process without rupturing the starch granule. Instead, the double helix molecules are believed to consist of one left-handed helix interlocked laterally with a right-handed helix and held by hydrogen bonding in a configuration resembling an interlocked zipper. The interlocking is so complete that the two helices appear to have a common axis. This structure is consistent with the theory that the helices retain their helical structure as they disengage. During the conversion to the single helix form, it is believed that the organic non-starch solvents enter the double helices, disrupt the hydrogen bonding, and become captured within the cavities of the single helices. These single helix inclusion complexes are relatively stable, possibly because the guest molecules reinforce the helical configuration of the host molecule. However, as described below, the sequestered solvent molecules are readily displaced by other molecules under the appropriate conditions, giving the starch hydrolysate compositions of this invention their unique properties.

2. Cleavage of Chain Segments

After the starch molecules have been converted to the single helical form, chain segments in the granular starch are cleaved from the amylopectin molecule. In general, the same processing conditions as in the first step are repeated in the second step with the exceptions that the temperature is preferably slightly lower and that the slurry is acidified to promote the cleavage of the chain segments at the location of branching (the $\alpha$-1,6-linkages). It is preferred that the temperature is about 50° to 150° C. and that the slurry is acidified to a Normality of about 0.05 to 2.0. It is feasible, and preferred, to simply adjust the temperature of the slurry and then add acid to the slurry to achieve the desired degree of cleavage. The processes described in Sugimoto, U.S. Pat. No. 3,799,805, issued Mar. 26, 1974, and in Eastman, U.S. patent application Ser. No. 07/884,693, filed May 18, 1992, now U.S. Pat. No. 5,275,837, each of which is incorporated by reference, are also suitable for cleaving the chain segments.

It is believed that the cleaved A-chain and B-chain segments in the single helix form are primarily responsible for the sequestering properties of the starch hydrolysates. These chain segments have a D.P. in the range of about 10 to 200 and a weight-average D.P. of about 10 to 50. At least about 20% of the starch is in this single-helical, narrow-D.P.-range form. From the point of view of maximizing yields, it is preferred that at least about 40% of the starch is in this form, and most preferred that the maximum amount feasible is in this form. However, as the percentage in this form increases, the likelihood that the starch granule will lose its integrity and that the recovered product will be in a non-granular form also increases. It is well known that granular starch is easier to handle than non-granular starch. Accordingly, there is a trade-off between yields and ease of processing. The amount of the starch in the sequestering form is a function of the efficiency of the conversion to the single helical form and of the efficiency of the cleavage. In other words, a 20% concentration of the sequestering form is achieved with, for example, either a relatively efficient conversion to the single helix form and a relatively inefficient cleavage, or vice versa. As the desired concentration increases, the efficiency of both steps becomes more important.

The percentage of the starch in this sequestering form can be further increased by various separation techniques, e.g., gel permeation chromatography which separates starch molecules based upon their size. By employing such techniques, the percentage of starch molecules in this form can be increased to 50%, 75%, or more. Such techniques can also be used to enrich a narrower molecular size. However, present separation techniques are effective only with non-granular materials. Accordingly, if the starch is not already non-granular, it is necessary to rupture the granule before employing such separation techniques.

3. Uses As Sequesterers

The starch hydrolysates of this invention are particularly suited for use as sequesterers. Like the cyclodextrins, they exhibit a hydrophilic outer surface and a hydrophobic inner cavity. Their inner cavity has a diameter of approximately 1 to 3 Angstroms and a length of approximately 10 to 250 Angstroms. The length depends, of course, on the D.P. of the molecule (based on a period of 8 Angstroms between repeating units of 6 anhydroglucose units). Both the diameter and length may increase to accommodate some lipophilic guest molecules. The hydrophobicity of the helix depends, in part, on the amount and type of chemical substitution. Unlike the cyclodextrins, these variable properties provide the starch hydrolysates of this invention with the capability of sequestering a wide variety of sizes, shapes, and hydrophobicities of guest molecules. In turn, this capability enables these starch hydrolysates to be used in most of the applications where cyclodextrins have been used and, in addition, to be used in many other applications.

In the agrichemical area, these sequesterers are used as powderizers for liquids and gases; as stabilizers of chemicals and vitamins; as volatility reducers; as emulsifiers; as controlled release agents; as solubility-altering agents; as bioavailability enhancers; as dose-efficiency enhancers; and as pesticide toxicity reducers.

In the food area, these sequesterers are used as stabilizers for colors, flavors, vitamins, and spices; as agents to reduce or eliminate the evaporation of flavor oils; as mask agents for odors and tastes; as breath fresheners; as foaming power enhancers; as anti-caking agents; as separators for food components; and as removers of bitter tasting components.

In the pharmaceutical area, the sequesterers are used as powderizers for oily and low-melting substances; as combiners for incompatible drugs; as drug stabilizers; as reducers of toxicity and volatility; as improvers of taste, odor, and color; as bioavailability improvers for ingestibles, injectables, implants, and topicals; and as tissue irritant reducers.

Other uses of these sequesterers include as chromatography agents; as isomer separators; as agents in stereoselective reactions; as concentrators of trace materials; as catalysts; as water purifiers; as flavor release controllers in chewing gum; as aflatoxin sequesterers; as cholesterol removers; as protectors of delicate molecules during frying, baking, etc.; as browning inhibitors in fresh fruit; and as precursors in the preparation of alkyl polyglycosides.

I claim:

1. A method of preparing a starch hydrolysate composition particularly suited for use as a sequesterer, the method comprising:
 (a) obtaining a granular starch containing at least about 30% amylopectin;
 (b) preparing a slurry of about 10 to 50% of the granular starch in a liquid medium which comprises about 60 to 90% of an organic non-starch solvent and about 10 to 40% of a starch solvent;
 (c) heating the slurry under conditions sufficient to convert at least a portion of the amylopectin molecules to the form of single helical inclusion complexes of starch molecules holding one or more of the non-starch solvent molecules as the initial guest molecules within their internal cavities;
 (d) heating the slurry under conditions sufficient to cleave enough chain segments from the amylopectin molecules such that at least about 20% of the starch is in a sequestering form comprising single helical inclusion complexes of starch molecules having a D.P. of about 10 to 200 and a weight-average D.P. of about 10 to 50 as the host molecules holding one or more first guest molecules within their internal cavities; and
 (e) separating the resulting starch from the liquid.

2. The method of claim 1 wherein the resulting starch is in a granular form.

3. The method of claim 1 wherein the resulting starch is in a non-granular form.

4. The method of claim 1 wherein the initial granular starch contains at least about 50% amylopectin.

5. The method of claim 1 wherein the initial granular starch contains at least about 90% amylopectin.

6. The method of claim 1 wherein the organic non-starch solvent comprises acetone, methanol, ethanol, n-propanol, or isopropanol; and the starch solvent comprises water, dimethyl sulfoxide, dimethyl formamide, N-methyl pyrrolidone, or 2-amino ethanol.

7. The method of claim 6 wherein the conversion to the single helical form is conducted at a temperature of about 70° to 180° C., a pressure of about 1 to 20 atmospheres, and an acidified slurry Normality of less than about 1.5.

8. The method of claim 7 wherein the cleavage of chain segments from the amylopectin molecules is conducted at a temperature of about 50° to 150° C. and an acidified slurry Normality of about 0.05 to 2.0.

9. A method for preparing a starch hydrolysate sequesterer said method comprising the steps of heating a slurry of granular starch comprising at least 30% amylopectin in a liquid medium comprising about 10–40% water and about 90–60% of a water miscible non-starch solvent to form a slurry of starch granules which when viewed under polarized light do not exhibit the characteristic Maltese Cross pattern of birefringence, and heating the slurry of starch granules in the presence of an acid until at least 20% of the starch in the granules has a D.P of about 10 to about 200.

10. The method of claim 9 further comprising the step of disintegrating the granules to produce a non-granular starch hydrolysate sequesterer.

* * * * *